(12) United States Patent
OBar

(10) Patent No.: US 12,396,536 B2
(45) Date of Patent: Aug. 26, 2025

(54) ELEVATOR EMERGENCY KIT DEVICE

(71) Applicant: Tammy OBar, Tuolumne, CA (US)

(72) Inventor: Tammy OBar, Tuolumne, CA (US)

( * ) Notice: Subject to any disclaimer, the term of this patent is extended or adjusted under 35 U.S.C. 154(b) by 37 days.

(21) Appl. No.: 18/488,417

(22) Filed: Oct. 17, 2023

(65) Prior Publication Data

US 2024/0130498 A1 Apr. 25, 2024
US 2024/0225223 A9 Jul. 11, 2024

Related U.S. Application Data

(60) Provisional application No. 63/418,736, filed on Oct. 24, 2022.

(51) Int. Cl.
*A61F 17/00* (2006.01)
*A45C 13/00* (2006.01)
*A45C 13/02* (2006.01)
*A45C 11/00* (2006.01)

(52) U.S. Cl.
CPC ............ *A45C 13/02* (2013.01); *A45C 13/005* (2013.01); *A61F 17/00* (2013.01); *A45C 2011/007* (2013.01)

(58) Field of Classification Search
CPC . A45C 13/02; A45C 13/005; A45C 2011/007; A61F 17/00
USPC ........................................ 206/223, 570, 571
See application file for complete search history.

(56) References Cited

U.S. PATENT DOCUMENTS

| | | | |
|---|---|---|---|
| 3,387,698 A | 6/1968 | Klaas | |
| 4,844,373 A * | 7/1989 | Fike, Sr. ............... | B65H 49/322 242/596.4 |
| 5,848,700 A | 12/1998 | Horn | |
| 5,931,304 A | 8/1999 | Hammond | |
| 6,116,426 A * | 9/2000 | Slonim .................. | A61B 50/31 206/499 |
| 6,206,192 B1 * | 3/2001 | Winstead ............... | A61C 19/02 206/572 |
| 6,422,669 B1 * | 7/2002 | Salvatori ............. | A61N 1/3968 206/320 |
| 6,454,097 B1 * | 9/2002 | Blanco ..................... | A45C 3/02 206/570 |
| 8,286,794 B1 * | 10/2012 | Agadzi .................. | A61B 50/33 220/8 |
| 8,647,123 B1 * | 2/2014 | Carter .................... | G16H 40/63 434/262 |
| 9,286,440 B1 | 3/2016 | Carter | |
| 11,696,859 B2 * | 7/2023 | DeLisle ................. | B65D 27/06 206/570 |

(Continued)

*Primary Examiner* — Jacob K Ackun
(74) *Attorney, Agent, or Firm* — Brennan, Manna & Diamond, LLC

(57) ABSTRACT

An elevator emergency kit device is disclosed that provides the necessary items for a person who is trapped in an elevator to survive. The elevator emergency kit device comprises a body component that is configured in a rectangular, box-like shape that contains a cavity for storing a plurality of emergency items and a lid that secures to the body component. The plurality of emergency items can include, but is not limited to, bottles of water, first aid items, a flashlight, a urine pouch with a screw-type lid, a power bank for charging cell phones, sugar and sugar-free candy, etc. Generally, the body component is secured to a wall of the elevator, either directly or by being inserted into a small, plastic box secured to the elevator wall.

11 Claims, 4 Drawing Sheets

(56) References Cited

U.S. PATENT DOCUMENTS

| | | | | |
|---|---|---|---|---|
| 2002/0157972 | A1* | 10/2002 | Gallo | A61J 1/00 |
| | | | | 206/570 |
| 2004/0262190 | A1* | 12/2004 | Bud | A62B 3/00 |
| | | | | 206/570 |
| 2006/0289329 | A1* | 12/2006 | Miller | B65D 75/245 |
| | | | | 206/570 |
| 2008/0078682 | A1* | 4/2008 | Clark | A62B 99/00 |
| | | | | 206/223 |
| 2008/0308451 | A1* | 12/2008 | Riechel | A61F 17/00 |
| | | | | 206/581 |
| 2011/0297147 | A1* | 12/2011 | Lick | A61B 50/31 |
| | | | | 128/202.16 |
| 2014/0069827 | A1* | 3/2014 | Thede | B65D 85/00 |
| | | | | 206/223 |
| 2014/0311944 | A1* | 10/2014 | Michaels | G09B 19/24 |
| | | | | 206/570 |
| 2019/0043615 | A1* | 2/2019 | Subbarao | G16H 40/63 |
| 2023/0124963 | A1* | 4/2023 | Laskin | A45C 5/065 |
| | | | | 206/570 |

* cited by examiner

ELEVATOR EMERGENCY KIT DEVICE

CROSS-REFERENCE TO RELATED APPLICATION

The present application claims priority to, and the benefit of, U.S. Provisional Application No. 63/418,736, which was filed on Oct. 24, 2022, and is incorporated herein by reference in its entirety.

FIELD OF THE INVENTION

The present invention relates generally to the field of elevator emergency kit devices. More specifically, the present invention relates to an emergency kit capable of offering several necessities if a person is stuck in an elevator. Accordingly, the present disclosure makes specific reference thereto. Nonetheless, it is to be appreciated that aspects of the present invention are also equally applicable to other like applications, devices, and methods of manufacture.

BACKGROUND

By way of background, this invention relates to improvements in elevator emergency kit devices. Generally, people riding in an elevator can be at constant risk for getting stuck. Some people may get stuck in the elevator for long periods of time until power can be restored, the elevator can get fixed, or the person can get rescued. Furthermore, there are typically no supplies in the elevator, and people may lack food, water, a place to use the bathroom, lose cell phone battery, etc.

Further, most elevators do not contain such an emergency kit. Accordingly, when people are trapped inside the elevator, they may have no recourse if exhibiting an emergency. For example, if a person is trapped in an elevator and has to use the restroom and/or has low blood sugar and doesn't have anything to eat. These emergencies can cause the wait time of being stuck in an elevator to feel interminable. Accordingly, people trapped in an elevator may require various resources.

Accordingly, there is a demand for an improved elevator emergency kit device that offers several necessities if a person is stuck in an elevator. More particularly, there is a demand for an elevator emergency kit device that ensures people can remain comfortable in the elevator until rescued or power is restored.

Therefore, there exists a long-felt need in the art for an elevator emergency kit device that provides users with an emergency kit capable of offering several necessities if a person is stuck in an elevator. There is also a long-felt need in the art for an elevator emergency kit device that enables users to easily retrieve the kit from a mounted storage box within the elevator. Further, there is a long-felt need in the art for an elevator emergency kit device that includes numerous items helpful for surviving a period of time while being stuck in the elevator like food, multiple water bottles, a means for light, a urination bag, a perforated area on the top that can be pressed down and used as a porta-potty, etc. Moreover, there is a long-felt need in the art for a device that ensures people can remain comfortable in the elevator until rescued or power is restored. Further, there is a long-felt need in the art for an elevator emergency kit device that is stored in a small plastic box. Finally, there is a long-felt need in the art for an elevator emergency kit device that can be mounted on the wall of an elevator for easy accessibility.

The subject matter disclosed and claimed herein, in one embodiment thereof, comprises an elevator emergency kit device. The device is an emergency kit filled with the necessary items for a person who is trapped in an elevator to survive. The elevator emergency kit device comprises a body component that is configured in a rectangular, box-like shape that contains a cavity for storing a plurality of emergency items and a lid that secures to the body component. The plurality of emergency items can include, but is not limited to, bottles of water, first aid items, a flashlight, a urine pouch with a screw-type lid, a power bank for charging cell phones, sugar and sugar-free candy, etc. Further, the body component can also have a perforated area on the top of the lid that can be pressed down on and removed, to be used as a porta-potty over the urine pouch. Generally, the body component is secured to a wall of the elevator, either directly or by being inserted into a small, plastic box secured to the elevator wall.

In this manner, the elevator emergency kit device of the present invention accomplishes all of the foregoing objectives and provides users with a device that offers several necessities if a person is stuck in an elevator. The device is a rectangular structure that stores the plurality of emergency items. The device can be manufactured of a plastic or metal material.

SUMMARY OF THE INVENTION

The following presents a simplified summary in order to provide a basic understanding of some aspects of the disclosed innovation. This summary is not an extensive overview, and it is not intended to identify key/critical elements or to delineate the scope thereof. Its sole purpose is to present some general concepts in a simplified form as a prelude to the more detailed description that is presented later.

The subject matter disclosed and claimed herein, in one embodiment thereof, comprises an elevator emergency kit device. The device is an emergency kit filled with the necessary items for a person who is trapped in an elevator to survive. The elevator emergency kit device comprises a body component that is configured in a rectangular, box-like shape that contains a cavity for storing a plurality of emergency items and a lid that secures to the body component. The plurality of emergency items can include, but is not limited to, bottles of water, first aid items, a flashlight, a urine pouch with a screw-type lid, a power bank for charging cell phones, sugar and sugar-free candy, etc.

In one embodiment, the elevator emergency kit device relates to an emergency kit for use in an elevator that contains resources for assistance for elevator emergencies, such as hunger, thirst, low blood sugar, power outage, cell phone needs charged, bathroom emergencies, etc., or any other suitable elevator emergencies as is known in the art.

Generally, elevator systems are characterized in that each elevator cab is equipped with an emergency call device that is directly or indirectly connected to a central control station. In an emergency, a person in need of assistance communicates a message via the automatic, emergency call device to the manned control station. The control station receives the emergency call and executes assistance according to an alarm plan specific to the type of emergency. The danger exists that people trapped in the elevator may need emergency assistance.

Accordingly, the objective of the invention is to provide an emergency kit device for use in the elevator with which the person(s) trapped in the elevator can promptly obtain resources for assistance, while waiting on the control station for assistance. In one embodiment, the elevator emergency kit device comprises a body component that is configured in a rectangular, box-like shape that contains a cavity for storing a plurality of emergency items and a lid component that secures to the body component. The body component can be any suitable shape and size as is known in the art, depending on the wants and/or needs of a user and how many emergency items are being held within the body component. Furthermore, the cavity of the body component comprises a plurality of dividers which break up the cavity into multiple compartments for storing and organizing the plurality of emergency items. The lid component typically mirrors the shape and size of the body component to secure the contents of the body component.

In one embodiment, the lid component is placed on the body component and secured at either end or at all four ends via a latch, clasp and/or lock. In another embodiment, the lid component comprises a set of hinges on one side to allow the lid component to open and close on its hinges. In either embodiment, the lid component comprises a lock or enabling mechanism that prevents users from opening the lid component and accessing the contents of the device. In this embodiment, the lock or enabling mechanism is only released or unlocked, when the elevator is not functioning and has stalled. Specifically, in an elevator emergency, a signal is transmitted via an emergency connection device located on the lid component, to the central control station so that it automatically activates the lock or enabling mechanism. The lock or enabling mechanism comprises a magnetic lock, a sliding pin lock, etc. This prevents the emergency kit device from being opened and prevents the emergency items from being randomly removed at any time while the elevator is being normally operated. Typically, the emergency connection device would also have an emergency battery backup system when loss of power occurs.

In one embodiment, the body component of the elevator emergency kit device according to the invention preferably has multiple compartments and contains various resources (i.e., emergency items) for assistance that are needed in an emergency, such as glucose, water bottles, snacks, sugar and sugar-free candy, a power bank to charge a cell phone, cold packs, whistles, handkerchiefs, chewing gum, oxygen masks, urine pouches, flashlights and/or first aid items. Individual meal rations and/or MRE's (meal ready-to-eat) can also be stored in the emergency kit device.

In one embodiment, because the situation of being trapped in an elevator cab is quite dangerous, especially for people that suffer from illnesses such as diabetes, asthma, and allergies, it is advantageous for the emergency kit device to contain non-prescription medications for diabetics, allergy sufferers or for people who suffer from asthma, etc., or any other suitable non-prescription medications. Specifically, such medications can include, but are not limited to, insulin, alpha glucosidase inhibitors, sulfonylureas, biguanides, glinides, insulin sensitizers (gloxazones), incretin mimetics and dipeptidyl peptidase 4 inhibitors, SGLT2 inhibitors, and/or amylin analogs which can be stored in the emergency kit device as medications for diabetics. Salbutamol, ipratropium bromide and xanthine can be stored in the emergency kit device as medications for persons suffering from asthma. Moreover, the emergency kit device can also be equipped with a blood sugar measuring device with accessories (i.e., lancing device, lancet, measuring strips, etc.), glucose solution for diabetics (glucose solution in tubes, etc.), asthma spray, fire resistant thermal blankets, card games, books and/or a mobile phone. For the mobile telephone, an intelligent charging device is installed in the kit device that regularly provides booster charging of the rechargeable battery of the phone.

In one embodiment, the emergency kit device comprises a urine pouch for use if a user trapped in the elevator needs to use the restroom. Further, the lid component can comprise a perforated area on its top surface. The perforated area can then be pressed down on and removed, so that the lid can be placed over top the urine pouch, to serve as a porta-potty for adults and children trapped within the elevator.

In one embodiment, the emergency kit device is retrofitted in an existing elevator or integrated in an elevator to be newly constructed. Specifically, the body component is secured directly to a wall of the elevator via any suitable securing means as is known in the art, such as adhesives, screws, Velcro, etc. In another embodiment, a small, plastic box or sleeve is secured directly to the elevator wall for retaining the elevator emergency kit device. The box or sleeve would be secured via adhesives, screws, Velcro, etc., or any other suitable securing means as is known in the art. The small, plastic box or sleeve is sized and shaped to retain the emergency kit device. The sleeve would be rectangularly shaped to define a cavity, with a front wall, a back wall, a bottom surface, and opposing right and left walls, with an open top surface allowing access to the cavity, such that the emergency kit device can be easily slid in and out of for storage and use.

In yet another embodiment, the elevator emergency kit device comprises a plurality of indicia.

In yet another embodiment, a method of providing several necessities to people trapped in an elevator is disclosed. The method includes the steps of providing an elevator emergency kit device comprising a body component that is a rectangular, box-like structure with a lid component. The method also comprises inserting a plurality of emergency items into the body component, such as water bottles, snacks, a flashlight, a urine pouch, a power bank for cell phones, sugar and sugar-free candy, etc. Further, the method comprises securing the lid component to the body component. Finally, the method comprises mounting the body component to a wall of the elevator for easy accessibility.

Numerous benefits and advantages of this invention will become apparent to those skilled in the art to which it pertains, upon reading and understanding the following detailed specification.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and are intended to include all such aspects and their equivalents. Other advantages and novel features will become apparent from the following detailed description when considered in conjunction with the drawings.

BRIEF DESCRIPTION OF THE DRAWINGS

The description refers to provided drawings in which similar reference characters refer to similar parts throughout the different views, and in which.

DETAILED DESCRIPTION OF THE PRESENT INVENTION

Figure 1:
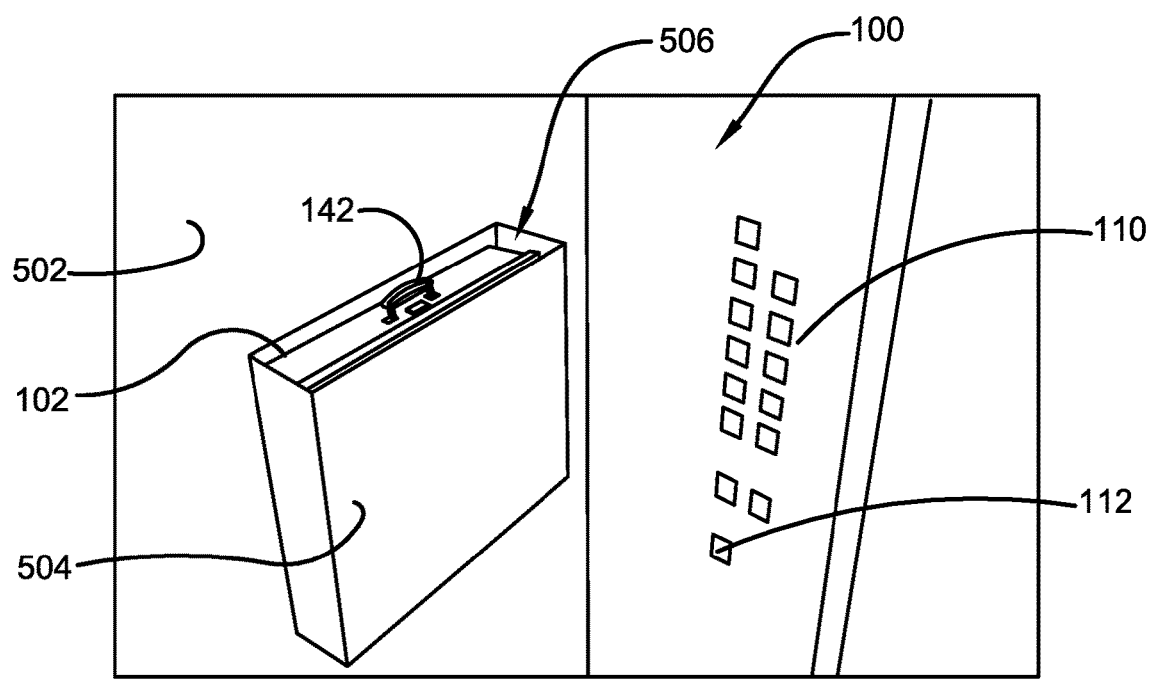
FIG. 1 illustrates a perspective view of one embodiment of the elevator emergency kit device of the present invention showing the device stored within a mounted box in the elevator in accordance with the disclosed architecture.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof. Various embodiments are discussed hereinafter. It should be noted that the figures are described only to facilitate the description of the embodiments. They are not intended as an exhaustive description of the invention and do not limit the scope of the invention. Additionally, an illustrated embodiment need not have all the aspects or advantages shown. Thus, in other embodiments, any of the features described herein from different embodiments may be combined.

As noted above, there is a long-felt need in the art for an elevator emergency kit device that provides users with an emergency kit capable of offering several necessities if a person is stuck in an elevator. There is also a long-felt need in the art for an elevator emergency kit device that enables users to easily retrieve the kit from a mounted storage box within the elevator. Further, there is a long-felt need in the art for an elevator emergency kit device that includes numerous items helpful for surviving a period of time while being stuck in the elevator like food, multiple water bottles, a means for light, a urination bag, a perforated area on the top that can be pressed down and used as a porta-potty, etc. Moreover, there is a long-felt need in the art for a device that ensures people can remain comfortable in the elevator until rescued or power is restored. Further, there is a long-felt need in the art for an elevator emergency kit device that is stored in a small plastic box. Finally, there is a long-felt need in the art for an elevator emergency kit device that can be mounted on the wall of an elevator for easy accessibility.

The present invention, in one exemplary embodiment, is a novel elevator emergency kit device. The device is an emergency kit filled with the necessary items for a person who is trapped in an elevator to survive. The elevator emergency kit device comprises a body component that is configured in a rectangular, box-like shape that contains a cavity for storing a plurality of emergency items and a lid that secures to the body component. The plurality of emergency items can include, but is not limited to, bottles of water, first aid items, a flashlight, a urine pouch with a screw-type lid, a power bank for charging cell phones, sugar and sugar-free candy, etc. Generally, the body component is secured to a wall of the elevator, either directly or by being inserted into a small, plastic box secured to the elevator wall. The present invention also includes a novel method of providing several necessities to people trapped in an elevator. The method includes the steps of providing an elevator emergency kit device comprising a body component that is a rectangular, box-like structure with a lid component. The method also comprises inserting a plurality of emergency items into the body component, such as water bottles, snacks, a flashlight, a urine pouch, a power bank for cell phones, sugar and sugar-free candy, etc. Further, the method comprises securing the lid component to the body component. Finally, the method comprises mounting the body component to a wall of the elevator for easy accessibility.

Referring initially to the drawings, FIG. 1 illustrates a perspective view of one embodiment of the elevator emergency kit device 100 of the present invention. In the present embodiment, the elevator emergency kit device 100 is an improved elevator emergency kit device 100 that provides a user 108 with an emergency kit filled with the necessary items for a person 108 who is trapped in an elevator 110 to survive. Specifically, the elevator emergency kit device 100 comprises a body component 102 with a lid component 104 and a plurality of emergency items 106 secured within, for access by a user 108 trapped in an elevator 110. The plurality of emergency items 106 can include, but is not limited to, bottles of water, first aid items, a flashlight, a urine pouch with a screw-type lid, a power bank for charging cell phones, sugar and sugar-free candy, etc.

Overall, the elevator emergency kit device 100 relates to an emergency kit for use in an elevator 110 that contains resources (i.e., emergency items 106) for assistance for elevator emergencies, such as hunger, thirst, low blood sugar, power outage, cell phone needs charged, bathroom emergencies, etc., or any other suitable elevator emergencies as is known in the art.

Generally, elevator systems are characterized in that each elevator cab 110 is equipped with an emergency call device 112 that is directly or indirectly connected to a central control station (not shown). In an emergency, a person 108 in need of assistance communicates a message via the automatic, emergency call device 112 to the manned control station. The control station receives the emergency call and executes assistance according to an alarm plan specific to the type of emergency occurring. The danger exists that people 108 trapped in the elevator 110 may need emergency assistance, which they can't obtain.

Accordingly, the object of the invention is to provide an emergency kit device 100 for use in the elevator 110 with which the persons 108 trapped in the elevator 110 can promptly obtain resources (i.e., emergency items 106) for assistance, while they are waiting on the control station for assistance. In one embodiment, the elevator emergency kit device 100 comprises a body component 102 that is configured in a rectangular, box-like shape that contains a cavity 114 for storing a plurality of emergency items 106 and a lid component 104 that secures to the body component 102. The body component 102 can be any suitable shape and size as is known in the art, depending on the wants and/or needs of a user 108 and how many emergency items 106 are being held within the body component 102. Furthermore, the cavity 114 of the body component 102 comprises a plurality of dividers 116 which break up the cavity 114 into multiple compartments 118 for storing and organizing the plurality of emergency items 106. The lid component 104 typically mirrors the shape and size of the body component 102 to secure the contents of the body component 102.

Furthermore, the lid component 104 is placed on the body component 102 and secured at either end 120 or at all four ends 120 and 122 via a latch 124, clasp and/or lock, or any other suitable securing means as is known in the art. In another embodiment, the lid component 104 comprises a set of hinges 126 on one side 120 to allow the lid component 104 to open and close on its hinges 126. The lid component 104 and body component 102 can also have a handle 142 for easy transport of the kit device 100.

Additionally, in one embodiment, the lid component 104 comprises a lock or enabling mechanism 128 that prevents users 108 from opening the lid component 104 and accessing the contents of the device 100. In this embodiment, the lock or enabling mechanism 128 is only released or unlocked when the elevator 110 is not functioning and has stalled. Specifically, in an elevator emergency, a signal is transmitted via an emergency connection device 130 located on the lid component 104, to the central control station so that it automatically activates the lock or enabling mechanism 128. The lock or enabling mechanism 128 comprises a magnetic lock, a sliding pin lock, etc. This prevents the emergency kit device 100 from being opened and prevents the emergency items 106 from being randomly removed at any time while the elevator 110 is being normally operated. Typically, the emergency connection device 130 would also have an emergency battery backup system 132 when loss of power occurs.

Figure 2:
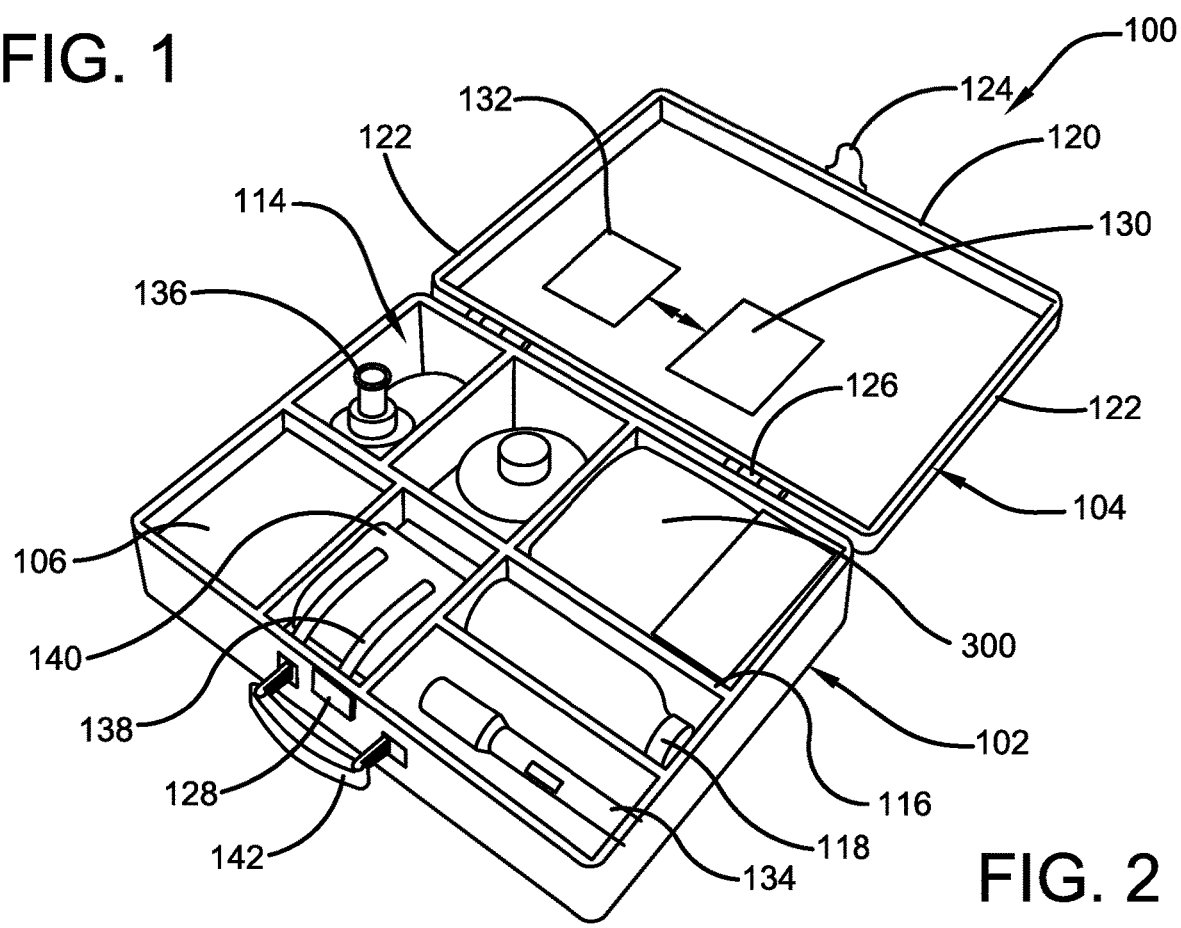
FIG. 2 illustrates a perspective view of one embodiment of the elevator emergency kit device of the present invention showing the emergency items stored within the kit in accordance with the disclosed architecture.
Figure 3:
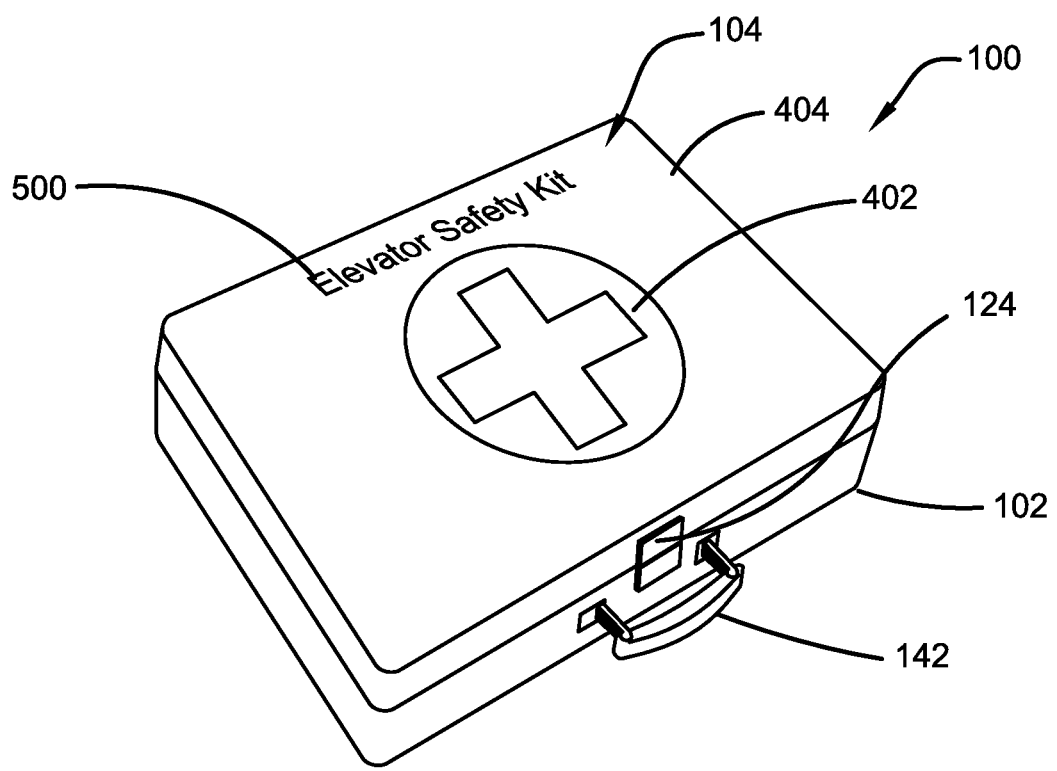
FIG. 3 illustrates a perspective view of one embodiment of the elevator emergency kit device of the present invention showing the emergency items removed from the kit in accordance with the disclosed architecture.

As shown in FIGS. 2-3, the body component 102 of the elevator emergency kit device 100 according to the invention, preferably has multiple compartments 118 and contains various resources (i.e., emergency items 106) for assistance that are needed in an emergency, such as glucose, water bottles, snacks, sugar and sugar-free candy, a power bank to charge a cell phone 138, cold packs, whistles, handkerchiefs, chewing gum, oxygen masks, urine pouches 400, flashlights and/or first aid items. Individual meal rations 300 and/or MRE's (meal ready-to-eat) can also be stored in the emergency kit device 100.

Furthermore, because the situation of being trapped in an elevator cab 110 is quite dangerous, especially for people that suffer from illnesses such as diabetes, asthma, and allergies, it is advantageous for the emergency kit device 100 to contain non-prescription medications 134 for diabetics, allergy sufferers or for people who suffer from asthma, etc., or any other suitable non-prescription medications 134. Specifically, such medications 134 can include, but are not limited to, insulin, alpha glucosidase inhibitors, sulfonylureas, biguanides, glinides, insulin sensitizers (gloxazones), incretin mimetics and dipeptidyl peptidase 4 inhibitors, SGLT2 inhibitors, and/or amylin analogs which can be stored in the emergency kit device 100 as medications for diabetics. Salbutamol, ipratropium bromide and xanthine can be stored in the emergency kit device 100 as medications for persons suffering from asthma. Moreover, the emergency kit device 100 can also be equipped with a blood sugar measuring device 136 with accessories (i.e., lancing device, lancet, measuring strips, etc.), glucose solution for diabetics (glucose solution in tubes, etc.), asthma spray, fire resistant thermal blankets, card games, books and/or a mobile phone 138. For the mobile telephone 138, an intelligent charging device 140 is installed in the kit device 100 that regularly provides booster charging of the rechargeable battery of the phone 138.

Figure 4:
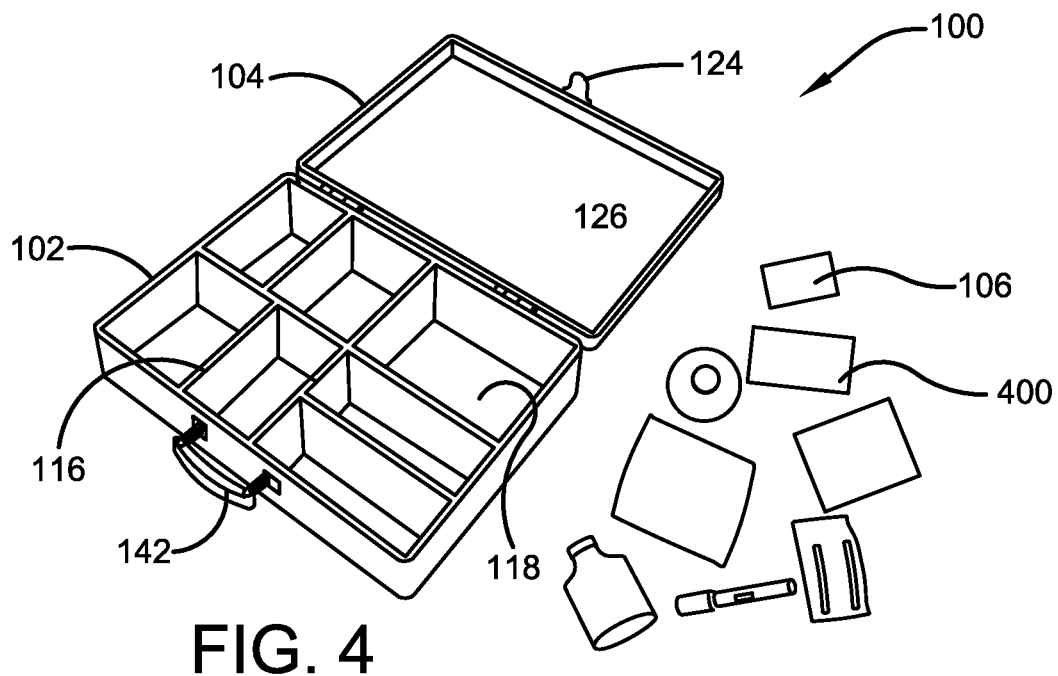
FIG. 4 illustrates a perspective view of one embodiment of the elevator emergency kit device of the present invention showing the lid of the kit in accordance with the disclosed architecture.

As shown in FIG. 4, the emergency kit device 100 comprises a urine pouch 400 for use if a user 108 trapped in the elevator 110 needs to use the restroom. Further, the lid component 104 can comprise a perforated area 402 on its top surface 404. The perforated area 402 can then be pressed down on and removed, so that the lid 104 can be placed over top the urine pouch 400, to serve as a porta-potty for adults 108 and children trapped within the elevator 110.

In yet another embodiment, the elevator emergency kit device 100 comprises a plurality of indicia 500. The body component 102 or lid component 104 of the device 100 may include advertising, a trademark, or other letters, designs, or characters, printed, painted, stamped, or integrated into the body component 102 or lid component 104, or any other indicia 500 as is known in the art. Specifically, any suitable indicia 500 as is known in the art can be included, such as but not limited to, patterns, logos, emblems, images, symbols, designs, letters, words, characters, animals, advertisements, brands, etc., that may or may not be elevator, emergency, or brand related.

Figure 5:
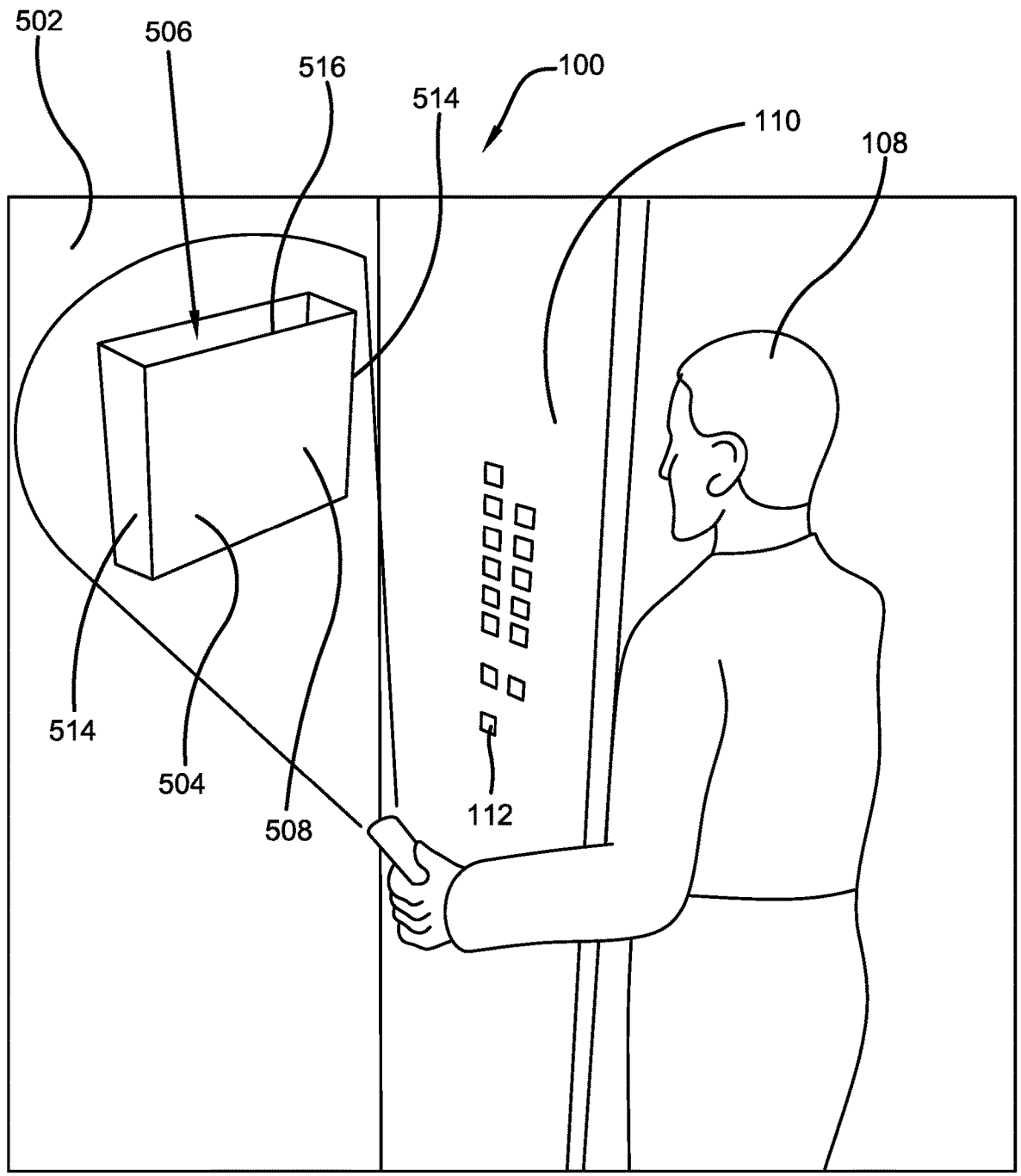
FIG. 5 illustrates a perspective view of one embodiment of the elevator emergency kit device of the present invention in use in accordance with the disclosed architecture.

As shown in FIG. 5, the emergency kit device 100 is retrofitted in an existing elevator 110 or integrated in an elevator 110 to be newly constructed. Specifically, the body component 102 is secured directly to a wall 502 of the elevator 110 via any suitable securing means as is known in the art, such as adhesives, screws, Velcro, etc. In another embodiment, a small, plastic box or sleeve 504 is secured directly to the elevator wall 502 for retaining the elevator 110 emergency kit device 100. The small, plastic box or sleeve 504 is sized and shaped to retain the emergency kit device 100. The sleeve 504 would be rectangularly shaped to define a cavity 506, with a front wall 508, a back wall 510, a bottom surface 512, and opposing right and left walls 514, with an open top surface 516 allowing access to the cavity 506, such that the emergency kit device 100 can be easily slid in and out of the cavity 506 for storage and use. Typically, the back wall 510 of the sleeve 504 is secured to the elevator wall 502. The back wall 510 of the box or sleeve 504 would be secured via adhesives, screws, Velcro, etc., or any other suitable securing means as is known in the art.

Figure 6:
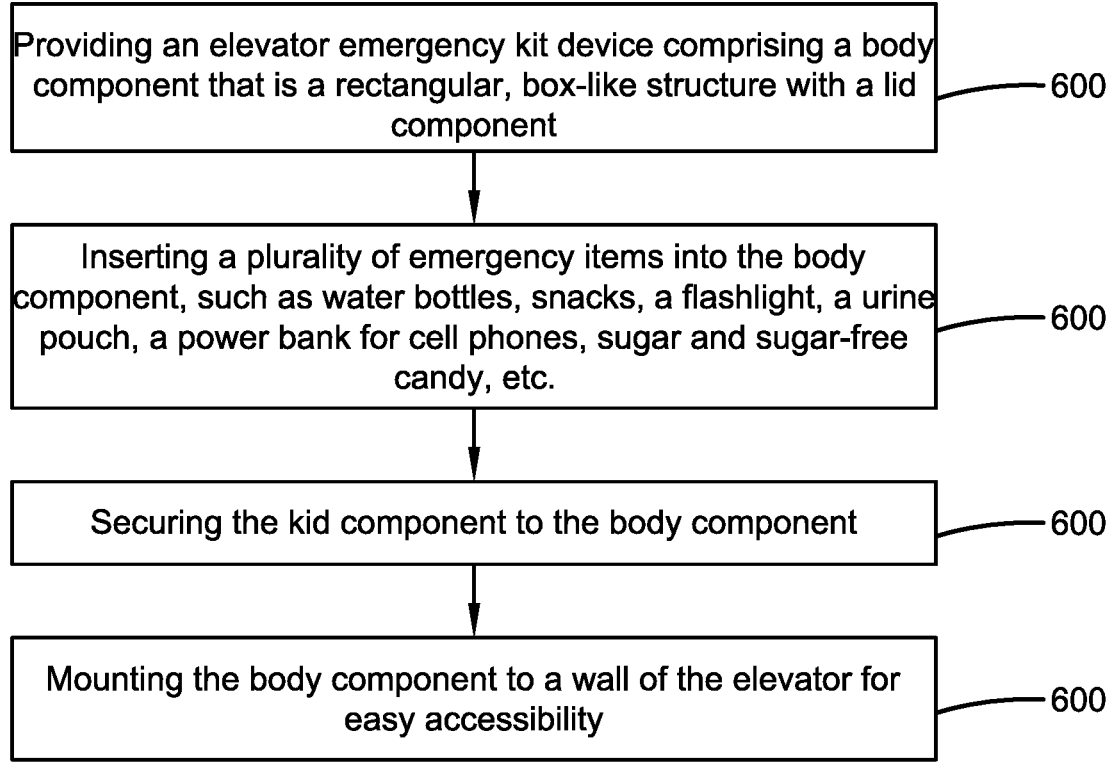
FIG. 6 illustrates a flowchart showing the method of providing several necessities to people trapped in an elevator in accordance with the disclosed architecture.

FIG. 6 illustrates a flowchart of the method of providing several necessities to people trapped in an elevator. The method includes the steps of at 600, providing an elevator emergency kit device comprising a body component that is a rectangular, box-like structure with a lid component. The method also comprises at 602, inserting a plurality of emergency items into the body component, such as water bottles, snacks, a flashlight, a urine pouch, a power bank for cell phones, sugar and sugar-free candy, etc. Further, the method comprises at 604, securing the lid component to the body component. Finally, the method comprises at 606, mounting the body component to a wall of the elevator for easy accessibility.

Certain terms are used throughout the following description and claims to refer to particular features or components. As one skilled in the art will appreciate, different users may refer to the same feature or component by different names. This document does not intend to distinguish between components or features that differ in name but not structure or function. As used herein "elevator emergency kit device", "emergency kit device", "emergency device", "kit device", and "device" are interchangeable and refer to the elevator emergency kit device 100 of the present invention.

Notwithstanding the foregoing, the elevator emergency kit device 100 of the present invention can be of any suitable size and configuration as is known in the art without affecting the overall concept of the invention, provided that it accomplishes the above-stated objectives. One of ordinary skill in the art will appreciate that the elevator emergency kit device 100 as shown in FIGS. 1-6 is for illustrative purposes only, and that many other sizes and shapes of the elevator emergency kit device 100 are well within the scope of the present disclosure. Although the dimensions of the elevator emergency kit device 100 are important design parameters for user convenience, the elevator emergency kit device 100 may be of any size that ensures optimal performance during use and/or that suits the user's needs and/or preferences.

Various modifications and additions can be made to the exemplary embodiments discussed without departing from the scope of the present invention. While the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. An elevator emergency kit device that provides a user with a kit filled with necessary items for a person who is trapped in an elevator, the elevator emergency kit device comprising:
    a body component;
    a lid component comprising a removable perforated section within a top surface of the lid;
    a urine pouch configured to fit under the removable perforated section portion of the lid component when removed so that the lid component and the urine pouch function as a porta-potty; and
    a plurality of emergency items;
    wherein the body component is configured to have a cavity;
    wherein the lid component secures on the body component to enclose the cavity;
    wherein the plurality of emergency items are retained within the cavity of the body component for use by a user trapped on an elevator; and
    wherein the body component is mounted within the elevator for use.

2. The elevator emergency kit device of claim 1, wherein the body component is configured in a rectangular, box-like shape that contains the cavity for storing the plurality of emergency items.

3. The elevator emergency kit device of claim 2, wherein the cavity of the body component comprises a plurality of dividers which break up the cavity into multiple compartments for storing and organizing the plurality of emergency items.

4. The elevator emergency kit device of claim 3, wherein the lid component comprises a set of hinges on one end to allow the lid component to open and close on the set of hinges.

5. The elevator emergency kit device of claim 1, wherein the plurality of emergency items comprise glucose, water bottles, snacks, sugar and sugar-free candy, a power bank to charge a cell phone, cold packs, whistles, handkerchiefs, chewing gum, oxygen masks, urine pouches, flashlights or first aid items.

6. The elevator emergency kit device of claim 5, wherein the plurality of emergency items can include non-prescription medications for people that suffer from illnesses such as diabetes, asthma and allergies.

7. The elevator emergency kit device of claim 6, wherein the body component is secured directly to a wall of the elevator.

8. The elevator emergency kit device of claim 6, wherein a sleeve is secured directly to the elevator wall and the emergency kit device is easily slid in and out of the sleeve for storage and use.

9. An elevator emergency kit device that provides a user with a kit filled with necessary items for a person who is trapped in an elevator, the elevator emergency kit device comprising:
    a body component configured in a rectangular, box-like shape that contains a cavity;
    a lid component sized and shaped to cover the body component, the lid component comprising a removable perforated section within a top surface of the lid;
    a urine pouch configured to fit under the removable perforated section portion of the lid component when removed so that the lid component and the urine pouch function as a porta-potty; and
    a plurality of emergency items;
    wherein the lid component secures on the body component to enclose the cavity via a sliding pin lock;
    wherein the lid component comprises a set of hinges on one end to allow the lid component to open and close on the set of hinges;
    wherein the plurality of emergency items are retained within the cavity of the body component for use by a user trapped on an elevator;
    wherein the cavity of the body component comprises a plurality of dividers which break up the cavity into multiple compartments for storing and organizing the plurality of emergency items;
    wherein the plurality of emergency items comprise glucose, water bottles, snacks, sugar and sugar-free candy, a power bank to charge a cell phone, cold packs, whistles, handkerchiefs, chewing gum, oxygen masks, urine pouches, flashlights or first aid items; and
    wherein a sleeve is secured directly to the elevator wall and the emergency kit device is easily slid in and out of the sleeve for storage and use; and
    wherein the lid component further comprises a signal transmitting component configured to send a signal to the sliding pin lock to open the sliding pin lock when an elevator emergency signal is received by the signal transmitting component.

10. The elevator emergency kit device of claim 9 further comprising a plurality of indicia.

11. The elevator emergency kit device of claim 9, wherein the plurality of emergency items can include non-prescription medications for people that suffer from illnesses such as diabetes, asthma and allergies.

* * * * *